US008372427B2

(12) United States Patent
Ludwig et al.

(10) Patent No.: US 8,372,427 B2
(45) Date of Patent: Feb. 12, 2013

(54) THERAPEUTIC COMPOSITION WITH ENHANCED ENDOTHELIUM TARGETING

(75) Inventors: Florian Niklas Ludwig, Mountain View, CA (US); Syed Faiyaz Ahmed Hossainy, Fremont, CA (US); Stephen Dirk Pacetti, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1424 days.

(21) Appl. No.: 11/714,439

(22) Filed: Mar. 5, 2007

(65) Prior Publication Data

US 2008/0220055 A1 Sep. 11, 2008

(51) Int. Cl.
*A61K 9/127* (2006.01)
*A61K 9/51* (2006.01)
(52) U.S. Cl. .................. 424/450; 424/499; 977/801
(58) Field of Classification Search .................. None
See application file for complete search history.

(56) References Cited

U.S. PATENT DOCUMENTS

| | | | |
|---|---|---|---|
| 5,292,524 A | 3/1994 | Male et al. | |
| 6,022,854 A | 2/2000 | Shuman | |
| 6,168,804 B1 | 1/2001 | Samuel et al. | |
| 6,258,378 B1 | 7/2001 | Schneider et al. | |
| 6,451,338 B1 | 9/2002 | Gregoriadis et al. | |
| 6,723,497 B2 | 4/2004 | Wolkers et al. | |
| 6,933,331 B2 | 8/2005 | Yadav et al. | |
| 7,049,140 B1 * | 5/2006 | Hallahan | 435/372 |
| 2003/0065355 A1 | 4/2003 | Weber | |
| 2003/0082224 A1 | 5/2003 | Noujaim et al. | |
| 2003/0093107 A1 | 5/2003 | Parsonage et al. | |
| 2003/0187496 A1 | 10/2003 | Kirk et al. | |
| 2003/0207975 A1 | 11/2003 | Yadav et al. | |
| 2003/0229184 A1 | 12/2003 | Acquarulo, Jr. et al. | |
| 2004/0058951 A1 | 3/2004 | Lanza et al. | |
| 2004/0215338 A1 | 10/2004 | Elkins et al. | |
| 2005/0038498 A1 | 2/2005 | Dubrow et al. | |
| 2005/0079179 A1 * | 4/2005 | Stewart et al. | 424/146.1 |
| 2005/0095267 A1 | 5/2005 | Campbell et al. | |
| 2005/0124976 A1 | 6/2005 | Devens, Jr. et al. | |
| 2005/0221072 A1 | 10/2005 | Dubrow et al. | |
| 2006/0159916 A1 | 7/2006 | Dubrow et al. | |
| 2006/0165926 A1 | 7/2006 | Weber | |
| 2006/0188543 A1 | 8/2006 | Feng | |
| 2008/0220055 A1 * | 9/2008 | Ludwig et al. | 424/450 |

FOREIGN PATENT DOCUMENTS

| | | |
|---|---|---|
| WO | WO 00/29029 | 5/2000 |
| WO | WO 0066182 A1 * | 11/2000 |
| WO | WO 03/047620 | 6/2003 |
| WO | WO 2007/025274 | 3/2007 |
| WO | WO 2007/145909 | 12/2007 |
| WO | WO 2008/013743 | 1/2008 |

OTHER PUBLICATIONS

Ding, B. et al., "Advanced Drug Delivery Systems That Target the Vascular Endothelium", Mol. Interventions, Apr. 2006, vol. 6: pp. 98-112.*
International Search Report for PCT/US2008/053707, mailed Sep. 1, 2008, 13 pgs.
George et al., "Platelet Surface Glycoproteins", Journal of Clinical Investigation, vol. 78, pp. 340-348, 1986.
Kieffer et al., "Dynamic redistribution of major platelet surface receptors after contact-induced platelet activation and spreading." An immunoelectron microscopy study, http://ajp.amjpathol.org/cgi/content/abstract/140/1/57 downlodaded May 18, 2007, 3 pgs.
Melero et al., "An Anti-ICAM-2 (CD102) Monoclonal Antibody Induces Immune-mediated Regression of Transplanted ICAM-2-negative Colon Carcinomas", Cancer Research 62, pp. 3167-3174, 2002.
Meroni et al., "Anti-endothelial cell antibodies: only for scientists or for clinicians too?" Clin. Exp. Immunol 104, pp. 199-202, 1996.
Peacock et al., "Bacterial fibronectin-binding proteins and endothelial cell surface fibronectin mediate adherence of *Staphylococcus aureus* to resting human endothelial cells", Microbiology 145, pp. 3477-3486, 1999.
Tiruppathi et al., "Isolation and characterization of a cell surface albumin-binding protein from vascular endothelial cells", Proc. Natl. Acad. Sci. USA, vol. 93, pp. 250-254, 1996.
Wikman et al., "Selection and characterization of HER2/neu-binding affibody ligands", Protein Engineering, Design & Selection vol. 17, No. 5 pp. 455-462, 2004.

* cited by examiner

*Primary Examiner* — Michael Burkhart
(74) *Attorney, Agent, or Firm* — Squire Sanders (US) LLP; Randy Shen, Esq.

(57) ABSTRACT

A composition that includes nanoparticles with binding affinity for platelets, and methods for using this composition to treat vascular disease are disclosed.

23 Claims, No Drawings

THERAPEUTIC COMPOSITION WITH ENHANCED ENDOTHELIUM TARGETING

FIELD OF THE INVENTION

The present invention relates to a therapeutic composition with enhanced endothelium targeting, and methods of using the composition for treating a vascular disease.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorbtion and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused agent's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents includes the targeted delivery of therapeutic agent-containing compositions. This method can consist of administering a composition containing a therapeutic agent and a targeting moiety designed to interact specifically with a biochemical entity present at, and exclusive to, the afflicted site in the vasculature.

The therapeutic agent-containing compositions can include nanoparticles. Nanoparticles, whose maximum linear dimension is no greater than about 400 nm, have the ability to penetrate a vessel wall. This ability provides an effective means to deliver a therapeutic agent at a disease site. However, a means to administer nanoparticles without losing a substantial fraction to the systemic circulation or to target nanoparticles to an endothelium is lacking in the art.

The present invention provides a nanoparticle-containing composition with enhanced endothelium targeting and a method of using the composition for the treatment of vascular disease.

SUMMARY OF THE INVENTION

The present invention relates to a composition that includes a plurality of nanoparticles including a first functional group with binding affinity for platelets operatively coupled to a surface of the nanoparticles and an optional second functional group with binding affinity for endothelium likewise operatively coupled to the surface of the nanoparticles.

In various aspects, the first functional group includes one or more first peptides, first proteins, first oligonucleotides or any combination thereof. In one embodiment, the one or more first peptide is an antibody fragment. In another embodiment, the one or more first oligonucleotide is an aptamer. In other embodiments, the one or more first protein can be an affibody or an antibody. When the one or more first protein is an antibody it can be an anti-p selectin, an anti-platelet factor, an anti-glycoprotein Ia-IIa complex, an anti-glycoprotein Ib, an anti-glycoprotein IIIa, an anti-glycoprotein IIb-IIIa complex, an anti-glycoprotein IV, an anti-glycoprotein VI, an anti-von Willebrand factor, an anti-α-granule membrane glycoprotein, an anti-platelet endothelial cell adhesion molecule, an anti-CD 49b, an anti-PAR-1, an anti-ADP receptor, an anti-α2β1 integrin, an anti-α5β1 integrin, an anti-α6β1 integrin, an anti-αIIbβ3 integrin, an anti-TREM-like transcript-1, an anti-Eph kinase, an anti-ephrin, an anti-ITIM-containing receptor and an anti-thrombospondin, or any combination thereof.

In various aspects, the second functional group includes one or more second peptides, second proteins, second oligonucleotides or any combination thereof. In various embodiments, the one or more second peptide can be an antibody fragment or a peptide with an RGD sequence. In another embodiment, the one or more second oligonucleotide is an aptamer. In other embodiments, the one or more second protein can be an affibody or an antibody. When the one or more second protein is an antibody it can be an anti-intercellular adhesion molecule, an anti-vascular cellular adhesion molecule, an anti-platelet endothelial cell adhesion molecule, an anti-thrombomodulin, an anti-e-selectin, an anti-fibronectin, an anti-sialyl-Lewis[b]glycan, an anti-endothelial glycocalyx protein and an anti-cadherin, or any combination thereof.

In various aspects, the nanoparticles include a bioactive agent encapsulated within, adhered to a surface of or integrated into the structure of the nanoparticles.

In various aspects, the nanoparticles can include micelles, liposomes, polymersomes, hydrogel particles or polymer particles.

The nanoparticle can have a maximum linear dimension of 1000 nanometers.

The bioactive agent can be a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, a matrix metalloproteinase inhibitor or a tissue inhibitor of metalloproteinase.

In various aspects, the nanoparticles can include a biodegradable or bioerodable material. In various embodiments, the nanoparticles can biodegrade or bioerode within 1.0 second to 100 hours, within 10.0 seconds to 10 hours or within 1.0 minute to 1 hour.

In various aspects the nanoparticles can include an optional third functional group with binding affinity for vascular cell wall components operatively coupled to the surface of the nanoparticles.

In various aspects the third functional group includes one or more lipids, third peptides, third proteins, third oligonucleotides or any combination thereof. In various embodiments, the one or more lipids can include lipophilic molecules such as an oleic acid, a stearic acid or an oleate derivative. In one embodiment, the one or more third oligonucleotide can be an aptamer. In another embodiment, the one or more third peptide can be an antibody fragment. In further embodiments, the one or more third protein can be an affibody or an antibody. When the one or more third protein is an antibody it can be an anti-elastin, an anti-collagen, an anti-tissue factor, an anti-laminin or any combination thereof.

Another aspect of the present invention relates to a method for localizing nanoparticles to a blood vessel wall. The method involves providing a composition according to the invention and administering the composition to a blood vessel in a patient.

In various aspects, administering the composition to a blood vessel in a patient involves intraarterial delivery. In various embodiments, intraarterial delivery involves percutaneous transluminal coronary arterial delivery or using a catheter.

In one embodiment, the nanoparticles include a bioactive agent, thereby providing a means for treating a vascular disease in a patient.

In various aspects, a composition of the invention can further include platelets. In various embodiments, the platelets are autologous, allogenic or xenogenic.

Another aspect of the present invention relates to a method for localizing nanoparticles to a blood vessel wall. The method involves providing a composition of the invention that further includes platelets and administering the composition to a blood vessel in a patient.

In various aspects, administering the composition to a blood vessel in a patient involves intraarterial delivery. In various embodiments, intraarterial delivery involves percutaneous transluminal coronary arterial delivery or using a catheter.

In one embodiment, the nanoparticles include a bioactive agent, thereby providing a means for treating a vascular disease in a patient.

DETAILED DESCRIPTION OF THE INVENTION

In many instances, localized intravascular administration of therapeutic agents would comprise a significant improvement in the art. But there are special considerations that must be taken into account in the development of a localized, intravascular drug-delivery system. For example, the system should not promote clotting or thrombogenesis. Moreover, the system should take into account the fact that constant blood flow through the vasculature results in rapid dilution of the drug. The present invention provides a drug delivery system that can safely be delivered intravascularly and which can be specifically targeted to a disease site locale to release therapeutic agent for a desired amount of time.

The present invention provides a composition that includes a plurality of nanoparticles that include a first functional group with binding affinity for platelets operatively coupled to the nanoparticle's surface and an optional second functional group with binding affinity for endothelium also operatively coupled to the nanoparticle's surface. Driven by hemodynamics, platelets tend to populate the blood volume close to a vessel wall, whereas larger cells such as red or white blood cells tend to localize more in the center of the vessel lumen. Thus, by binding bioactive agent-loaded nanoparticles to platelets the composition of the invention will have the ability to specifically localize near a vessel wall, thereby providing a novel means for the targeted delivery of a bioactive agent to a vascular disease locale.

As used herein, "nanoparticle" refers to a microscopic particle, composed of one or more polymers, whose size in nanometers (nm) includes a maximum linear dimension of less than 1000 nanometers. As used herein, linear dimension refers to the distance between any two points on a nanoparticle as measured in a straight line. Nanoparticles of the present invention can be irregular, oblong, spindle, rod, discoid, pancake, cylindrical, red blood cell-like, spherical or substantially spherical in shape as long as their shape and size allow binding interactions with platelets.

As used herein, "substantially spherical" refers to a shape that is not perfectly spherical but has a generally spherical shape, e.g., an ellipsoid.

As used herein, a "polymer" refers to a molecule(s) composed of a plurality of repeating structural units connected by chemical bonds.

Several types and configurations of nanoparticles are encompassed by the present invention. For example, nanoparticles may be composed of a range of materials including, but not limited to, a biostable polymer, a bioabsorbable polymer or a combination thereof. Biostable refers to polymers that are not degraded in vivo, i.e., are not biodegradable. The terms bioabsorbable, biodegradable, and bioerodable, as well as absorbed, degraded and eroded are used interchangeably (unless the context shows otherwise) and refer to polymers that are capable of being degraded or absorbed after being delivered to a disease locale in a patient, e.g., when exposed to bodily fluids such as blood, and that can be gradually resorbed, absorbed, and/or eliminated by the body.

Nanoparticles of the present invention can include biodegradable and bioerodable materials that, after delivery, biodegrade or bioerode within 1.0 second to 100 hours, within 10.0 seconds to 10 hours or within 1 minute to 1 hour. Methods of forming nanoparticles with known degradation rates are known to those skilled in the art; see for example U.S. Pat. No. 6,451,338 to Gregoriadis et al., U.S. Pat. No. 6,168,804 to Samuel et al. and U.S. Pat. No. 6,258,378 to Schneider et al., which are hereby incorporated by reference in their entirety.

Suitable nanoparticles include micelles, liposomes, polymersomes, hydrogel particles and polymer particles.

As used herein, a "micelle" refers to a supramolecular aggregate of amphipathic molecules in an aqueous solution. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in an aqueous solution the hydrophilic moiety seeks to interact with the water while the hydrophobic moiety seeks to avoid the water, i.e., they aggregate at the surface of the water. Amphiphilic molecules that have this effect are known as "surfactants." When the CMC is reached surfactant molecules will self-assemble into spheres with the hydrophilic ends of the molecules facing out, that is, in contact with the water forming the micelle corona and with the hydrophobic "tails" facing toward the center of the of the sphere.

Bioactive agents suspended in the aqueous medium can be entrapped and solubilized in the hydrophobic center of micelles, which can result in an increase in the bioavailability as well as improving the stability in biological surroundings, thereby improving the pharmacokinetics and possibly decreasing the toxicity of the bioactive agent. In addition, because of their nanoscale size, generally from about 5 nm to about 50 nm, micelles have been shown to exhibit spontaneous accumulation in pathological areas with leaky vasculature and impaired lymphatic drainage, a phenomenon known as the Enhanced Permeability and Retention or EPR effect.

As used herein, a "liposome" refers to a compartment that is completely enclosed by a bilayer typically composed of phospholipids. Liposomes can be prepared according to standard techniques known to those skilled in the art. For example, without limitation, suspending a suitable lipid, e.g., phosphatidyl choline, in an aqueous medium followed by sonication of the mixture will result in the formation of liposomes. Alternatively, rapidly mixing a solution of lipid in ethanol-water, for example, by injecting a lipid through a needle into an agitated ethanol-water solution can form lipid vessicles. Liposomes can also be composed of other amphiphilic substances, e.g., shingomyelin or lipids containing poly(ethylene glycol) (PEG).

As used herein, a "polymersome" refers to di- or tri-block copolymers that are modified to form bilayer structures similar to liposomes. Depending on the length and composition of the polymers in the block copolymer, polymersomes can be substantially more robust that liposomes. In addition, the ability to control the chemistry of each block of the block copolymer permits tuning of the polymersome's composition to fit the desired application. For example, membrane thickness, i.e., the thickness of the bilayer structure, can be controlled by varying the chain length of the individual blocks. Adjusting the glass transition temperatures of the blocks will affect the fluidity and therefore the permeability of the membrane. Even the mechanism of agent release can be modified by altering the nature of the polymers.

Polymersomes can be prepared by dissolving the copolymer in an organic solvent, applying the solution to a vessel surface, and then removing the solvent, which leaves a film of the copolymer on the vessel wall. The film is then hydrated to form polymersomes. Dissolving the block copolymer in a solvent and then adding a weak solvent for one of the blocks, will also create polymersomes. Other means of preparing polymersomes are known to those skilled in the art and are within the scope of this invention.

Polymersomes can be used to encapsulate bioactive agents by including the bioactive agent in the water used to rehydrate the copolymer film. Osmotically driving the bioactive agent into the core of preformed polymersomes, a process known as force loading, may also be employed. Using a double emulsion technique, polymersomes of relative monodispersivity and high loading efficiency are possible. The technique involves using microfluidic technology to generate double emulsions comprising water droplets surrounded by a layer of organic solvent. These droplet-in-a-drop structures are then dispersed in a continuous water phase. The block copolymer is dissolved in the organic solvent and self-assembles into proto-polymersomes on the concentric interfaces of the double emulsion. Completely evaporating the organic solvent from the shell yields the actual polymersomes. This procedure allows fine control over the polymersome size. In addition, the ability to maintain complete separation of the internal fluids from the external fluid throughout the process allows extremely efficient encapsulation.

As used herein, a "hydrogel particle" refers to a crosslinked network of polymer chains that is absorbent but stable in an aqueous environment. Hydrogel particles can be used to encapsulate bioactive agents by methods known to those skilled in the art.

As used herein, a "polymer particle" refers to a solid or porous particle, in contrast to the shell structure of liposomes and polymersomes and the relatively open structures of hydrogel particles. Methods for adhering a bioactive agent to the surface of or integrating a bioactive agent into the structure of a polymer particle are known to those skilled in the art.

Polymers that may be used to prepare nanoparticles of this invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids.

Nanoparticles of this invention have a first functional group with binding affinity for platelets operatively coupled to a surface of the nanoparticles.

As used herein, "functional group" refers to a surface-expressed chemical moiety with binding affinity for a target molecule or cell wall component.

As used herein, "operatively coupled" refers to the attachment of a functional group to the surface of a nanoparticle through either direct or indirect means. For example, it is possible for a functional group to be directly attached to the surface of the nanoparticle by a portion of the functional group itself. Alternatively, it is possible that the functional group is attached to the surface of the nanoparticle via an intermediate component that couples the functional group with the surface of the nanoparticle. Such intermediate components are often referred to as linkers. Linkers are di-functional molecules that can have one moiety that chemically attaches to a nanoparticle and a second moiety that chemically attaches to a functional group. Any number of intermediate components are encompassed by the present invention, and are known to those skilled in the art.

Functional groups can be localized to the surface of the nanoparticle by anchoring them to the surface. For example, a functional group with affinity for endothelium can be covalently bonded to the hydrophilic end of an amphiphilic molecule, such as a phospholipid with a hydrophilic spacer region coupled to its headgroup, or an amphiphilic block co-polymer, such as PEG-PLA. These anchored functional groups may then be localized to the surface of a nanoparticle by co-incubation of the groups with pre-made nanoparticles, or by including these groups during the nanoparticle formulation process, methods of which are known to those skilled in the art.

The first functional group with binding affinity for platelets can include one or more first peptides, first proteins, first oligonucleotides or any combination thereof. When the first functional group is a peptide, it can be an antibody fragment, e.g., without limitation, a Fab fragment, with binding affinity for platelets. When the first functional group is an oligonucleotide, it can be an aptamer.

As used herein, an "aptamer" refers to an oligonucleic acid that has binding affinity for a specific target, e.g., without limitation, a protein, a nucleic acid, a specific whole cell or a particular tissue. Aptamers can be obtained by in vitro selection from a large random sequence pool of nucleic acids, although natural aptamers are also encompassed by the present invention. Other methods of producing aptamers are known to those skilled in the art and are within the scope of this invention.

When the first functional group is a first protein, it can be an affibody or an antibody.

As used herein, an "affibody" refers to a relatively small synthetic protein molecule that has high binding affinity for a target protein. Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since it's binding site is approximately equivalent in surface area to the binding site of an antibody.

When the first protein is an antibody, it can be selected from a group that includes an anti p-selectin, an anti-platelet factor, an anti-glycoprotein Ia-IIa complex, an anti-glycoprotein Ib, an anti-glycoprotein IIIa, an anti-glycoprotein IIb-IIIa complex, an anti-glycoprotein IV, an anti-glycoprotein VI, an anti-von Willebrand factor, an anti-α-granule membrane glycoprotein, an anti-platelet endothelial cell adhesion molecule, an anti-CD 49b, an anti-PAR-1, an anti-ADP receptor, an anti-α2β1 integrin, an anti-α5β1 integrin, an anti-α6β1 integrin, an anti-αIIbβ3 integrin, an anti-TREM-like transcript-1, an anti-Eph kinase, an anti-ephrin, an anti-ITIM-containing receptor and an anti-thrombospondin, or any combination thereof.

In addition to a first functional group with binding affinity for platelets operatively coupled to its surface, a nanoparticle of the invention can have an optional second functional group with binding affinity for endothelium operatively coupled to its surface.

The second functional group with binding affinity for endothelium can include one or more second peptides, second proteins, second oligonucleotides or any combination thereof. When the second functional group is a peptide, it can be a peptide with an RGD sequence or an antibody fragment, e.g., without limitation, a Fab fragment, with binding affinity for endothelium. When the second functional group is an oligonucleotide, it can be an aptamer.

When the second functional group is a protein, it can be an affibody or an antibody. When the protein is an antibody, it can be selected from a group that includes an anti-intercellular adhesion molecule, an anti-vascular cellular adhesion molecule, an anti-platelet endothelial cell adhesion molecule, an anti-thrombomodulin, an anti-e-selectin, an anti-fibronectin, an anti-sialyl-Lewis[b]glycan, an anti-endothelial glycocalyx protein and an anti-cadherin, or any combination thereof.

Nanoparticles of the present invention can also include an optional third functional group with binding affinity for vascular cell wall components operatively coupled to the nanoparticles' surface.

The third functional group can include one or more lipids, third peptides, third proteins, third oligonucleotides or any combination thereof. When the third functional group is a lipid, it can be an oleic acid, a stearic acid or an oleate derivative. When the third functional group is an oligonucleotide, it can be an aptamer.

When the third functional group is a peptide, it can be an antibody fragment, e.g., without limitation, a Fab fragment, with binding affinity for a vascular cell wall component.

When the third functional group is a protein, it can be an affibody or an antibody. When the protein is an antibody, it can be an anti-elastin, an anti-collagen, an anti-tissue factor, an anti-laminin or any combination thereof.

It is to be understood that nanoparticles of the present invention will necessarily include a first functional group, as described above, but may also optionally include a second functional group and/or a third functional group coupled to the surface of the nanoparticle, as described above.

Nanoparticles of this invention have a bioactive agent encapsulated within, adhered to the surface of, or integrated into its structure.

As used herein, "encapsulated within" means the bioactive agent is contained substantially within the outer surface of the nanoparticle.

As used herein, "adhered to the surface of" means the bioactive agent is covalently or non-covalently attached to the outer surface of the nanoparticle.

As used herein, "integrated into the structure of" means the bioactive agent is part of the chemical structure of the material forming the nanoparticle.

As used herein, a "bioactive agent" refers to any substance that is of medical or veterinary therapeutic or prophylactic utility.

A therapeutic bioactive agent refers to a bioactive agent that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to regress; or (4) alleviating one or more symptoms of the disease.

A bioactive agent also refers to an agent that, when administered to a patient, either prevents the occurrence of a disease or disorder or retards the recurrence of the disease or disorder. Such a bioactive agent is often referred to as a prophylactic bioactive agent.

Suitable bioactive agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Suitable antiallergic agents include, without limitation, permirolast potassium.

Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethyl-rapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics; antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics;

psychostimulants; sedatives; tranquilizers; naturally derived or genetically engineered lipoproteins; and restenoic reducing agents.

Preferred bioactive agents include corticosteroids, everolimus, zotarolimus, sirolimus, sirolimus derivatives, paclitaxel, bisphosphonates, ApoA1, mutated ApoA1, ApoA1 milano, ApoA1 mimetic peptides, ABC A1 agonists, anti-inflammatory agents, anti-proliferative agents, anti-angiogenic agents, matrix metalloproteinase inhibitors and tissue inhibitors of metalloproteinases.

The amount of bioactive agent in a nanoparticle will depend on the required minimum effective concentration (MEC) of the agent and the length of time over which it is desired that the MEC be maintained. For most bioactive agents the MEC will be known to, or readily derivable by, those skilled in the art from the literature. For experimental bioactive agents or those for which the MEC by localized delivery is not known, it can be empirically determined using techniques well-known to those skilled in the art.

In some embodiments, a composition of the present invention further includes platelets. The platelets can be autologous, allogenic or xenogenic in nature.

As used herein, "autologous" refers to platelets that are obtained from the organism in which the composition is to be administered.

As used herein, "allogenic" refers to platelets that are obtained from a different organism of the same species as that in which the composition is to be administered.

As used herein, "xenogenic" refers to platelets that are obtained from a different species than that in which the composition is to be administered.

Methods of isolating and purifying platelets are known to those skilled in the art.

Another aspect of the present invention relates to a method for localizing nanoparticles to a blood vessel wall that includes providing a composition of the present invention and administering the composition to a blood vessel in a patient.

Administering the composition to a blood vessel in a patient can include intraarterial delivery of the composition. In certain embodiments, administering the composition involves percutaneous transluminal coronary arterial delivery or using a catheter, including guiding, diagnostic and drug delivery catheters. In one embodiment, the nanoparticles can contain a bioactive agent, thereby providing a means for delivering a bioactive agent to a vascular disease locale in a patient.

As used herein, a "patient" refers to any organism that can benefit from the administration of a bioactive agent. In particular, patient refers to a mammal such as a cat, dog, horse, cow, pig, sheep, rabbit, goat or a human being.

As used herein, "treating" refers to the administration of a therapeutically effective amount of a bioactive agent to a patient known or suspected to be suffering from a vascular disease. Bioactive agents useful with this invention are described above. Presently preferred bioactive agents include a corticosteroid, everolimus, zotarolimus, sirolimus, sirolimus derivatives, paclitaxel, a bisphosphonate, ApoA1, a mutated ApoA1, ApoA1 milano, an ApoA1 mimetic peptide, an anti-inflammatory agent, an anti-proliferative agent, an anti-angiogenic agent, a matrix metalloproteinase inhibitor and a tissue inhibitor of metalloproteinase.

As used herein, a "therapeutically effective amount" refers to the amount of bioactive agent that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion. Further, while restenosis tends generally to occur at the same locus as a previous atherosclerotic lesion, it may not be exactly so, so a region of a segment of a vessel somewhat distant from the site of the initial atherosclerosis may in fact be the site of restenosis.

As used herein, a "vascular disease locale" refers to the location within a patient's body where an atherosclerotic lesion(s) is present, where restenosis may develop, the site of vulnerable plaque(s) or the site of a peripheral arterial disease.

An atherosclerotic lesion refers to a deposit of fatty substances, cholesterol, cellular waste products, calcium and/or fibrin on the inner lining or intima of an artery.

Restenosis refers to the re-narrowing or blockage of an artery at or near the site where angioplasty or another surgical procedure was previously performed to remove a stenosis.

Vulnerable plaque on the other hand is quite different from either atherosclerosis or restenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

As used herein, a peripheral arterial disease refers to a condition similar to coronary artery disease and carotid artery disease in which fatty deposits build up in the inner linings of the artery walls thereby restricting blood circulation, mainly in arteries leading to the kidneys, stomach, arms, legs and feet.

Another aspect of the present invention relates to a method for localizing nanoparticles to blood vessel wall that involves providing a composition of the invention that further includes platelets, as described above. Methods of administering the composition to a blood vessel in a patient are described above. In one embodiment, the nanoparticles can contain a bioactive agent, thereby providing a means for delivering a bioactive agent to a vascular disease locale in a patient.

The present invention provides compositions that contain bioactive agent-containing nanoparticles that have the ability to bind to platelets. This property allows the nanoparticles to effectively localize at or near a vessel wall. Specifically, due to their relatively small spherical shape, and driven by physiological hemodynamics, platelets localize predominately along the vessel wall. Thus, platelet-bound nanoparticles will be "pushed" to the side of the vessel, thereby accumulating at the vessel wall and the site of a vascular disease.

While not being bound to any particular theory, it is believed that the mechanism for the proceeding phenomenon relates to the flow of non-spherical shaped cells, i.e., red blood cells, and spherically shaped cells, e.g., platelets, through the vasculature. Direct observations of red blood cell paths have shown that human red blood cells migrate away from a vessel wall whereas more spherically shaped cells migrate towards the vessel wall. Several factors involved in this effect include the viscosity of the medium, i.e., the blood, the diameter of the blood vessel, the rotation of the cells, the size of the cells and the shape of the cells.

Once platelet-bound bioactive agent-containing nanoparticles are pushed to the vessel wall, the optional second functional group with binding affinity for endothelium can secure the nanoparticles to the vessel wall, thereby decreasing the amount of bioactive agent-containing nanoparticles lost to the systemic circulation. Indeed, the optional third functional group with binding affinity for other vascular cell wall components can also secure the nanoparticles to the vessel wall, in particular to vessel segments which have incomplete endothelium or which are denuded of endothelial cells.

Once the bioactive agent-loaded nanoparticles are localized to the endothelium, and in some cases effectively bound to the endothelium, due to the biodegradation of the nanoparticles, bioactive agent will be released, thereby providing a means for treating a vascular disease.

In certain embodiments, nanoparticles may possess triggered release capabilities, e.g., they may be heat-, sound- or light-sensitive. Thus, once nanoparticles are localized at a vessel wall, they can be triggered to release a bioactive agent(s) by heating, light activation, or ultrasound. This may be done locally through a catheter-based intervention by an external device able to produce localized heat within a body, e.g., focused microwave radiation, or globally, e.g., by inducing fever, although in this latter case, the bioactive agent would still be localized by localization of the drug carrier. Methods of forming nanoparticles with triggered release capabilities are known to those skilled in the art.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition comprising:
    a plurality of nanoparticles comprising:
        a first functional group operatively coupled to a surface of a nanoparticle of the plurality of nanoparticles, wherein the first functional group comprises one or more first peptides, and each of which binds a component of platelets; and
        a second functional group operatively coupled to a surface of the nanoparticle, wherein the second functional group comprises one or more second peptides, and each of which binds endothelium,
    wherein the nanoparticle further comprises a bioactive agent encapsulated within, adhered to a surface of or integrated into the structure of the nanoparticle, and
    wherein the bioactive agent is for treating a vascular disease in a patient and does not activate platelets or induce thrombosis.

2. The composition according to claim 1, wherein the one or more first peptides comprise an antibody fragment that binds a component of platelets.

3. The composition according to claim 1, wherein the one or more second peptides comprise an antibody fragment that binds endothelium.

4. The composition according to claim 1, wherein the nanoparticles comprise micelles, liposomes, polymersomes, hydrogel particles or polymer particles.

5. The composition according to claim 1, wherein the nanoparticle has a maximum linear dimension of 1000 nanometers.

6. The composition according to claim 1, wherein the bioactive agent is selected from the group consisting of a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, a matrix metalloproteinase inhibitor and a tissue inhibitor of metalloproteinase.

7. The composition according to claim 1, wherein the nanoparticles comprise a biodegradable or bioerodable material.

8. The composition according to claim 7, wherein the nanoparticles biodegrade or bioerode within 1.0 second to 100 hours.

9. The composition according to claim 8, wherein the nanoparticles biodegrade or bioerode within 10.0 seconds to 10 hours.

10. The composition according to claim 9, wherein the nanoparticles biodegrade or bioerode within 1.0 minute to 1 hour.

11. The composition according to claim 1, wherein the nanoparticle further comprises a third functional group that binds vascular cell wall components and is operatively coupled to a surface of the nanoparticle, and wherein the third functional group comprises one or more third peptides.

12. The composition according to claim 11, wherein the one or more third peptides comprise an antibody fragment.

13. The composition according to claim 12, wherein the antibody fragment is based on an antibody is selected from the group consisting of an anti-elastin, an anti-collagen, an anti-tissue factor, an anti-laminin, or any combination thereof.

14. A method for localizing nanoparticles to a blood vessel wall comprising;
    providing a composition according to claim 1; and
    administering the composition to a blood vessel in a patient.

15. The method according to claim 14, wherein administering the composition to a vessel in a patient comprises intraarterial delivery.

16. The method according to claim 15, wherein intraarterial delivery comprises percutaneous transluminal coronary arterial delivery.

17. The method according to claim 15, wherein intraarterial delivery comprises using a catheter.

18. The composition according to claim 1, further comprising platelets.

19. The composition according to claim 18, wherein the platelets are autologous, allogenic or xenogenic.

20. A method for localizing nanoparticles to a blood vessel wall comprising:
    providing a composition according to claim 18; and
    administering the composition to a blood vessel in a patient.

21. The method according to claim 20, wherein administering the composition to a blood vessel in a patient comprises intraarterial delivery.

22. The method according to claim 21, wherein intraarterial delivery comprises percutaneous transluminal coronary arterial delivery.

23. The method according to claim 21, wherein intraarterial delivery comprises using a catheter.

* * * * *